(12) United States Patent
Gaudoin et al.

(10) Patent No.: US 6,296,655 B1
(45) Date of Patent: *Oct. 2, 2001

(54) CATHETER BALLOON WITH BIASED MULTIPLE WINGS

(75) Inventors: Henri A. Gaudoin, Mountain View; Philip C. Foreman; Tri-Phuoc V. Le, both of San Jose, all of CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/067,450

(22) Filed: Apr. 27, 1998

(51) Int. Cl.[7] ........................................ A61M 25/10
(52) U.S. Cl. ............ 606/194; 604/103.14; 623/1.11; 606/108; 264/285; 264/339
(58) Field of Search ................... 606/194, 108, 606/192; 604/96, 103.14; 264/285, 299, 339; 623/1.11

(56) References Cited

U.S. PATENT DOCUMENTS

| | | |
|---|---|---|
| 3,050,066 | 8/1962 | Koehn ............................ 128/349 |
| 3,459,175 | 8/1969 | Miller ............................... 128/2 |
| 3,774,596 | 11/1973 | Cook ................................. 128/5 |
| 4,141,364 | 2/1979 | Schultze ..................... 128/349 B |
| 4,261,339 | 4/1981 | Hanson et al. .................. 128/1 D |
| 4,276,874 | 7/1981 | Wolvek et al. .................. 128/1 D |
| 4,346,698 | 8/1982 | Hanson et al. .................. 128/1 D |
| 4,406,656 | 9/1983 | Hattler et al. ................... 604/280 |
| 4,576,142 | 3/1986 | Schiff .............................. 128/1 D |
| 4,655,745 | 4/1987 | Corbett ............................. 604/49 |
| 4,681,092 | 7/1987 | Cho et al. ........................ 128/1 D |
| 4,762,130 | 8/1988 | Fogarty et al. ................ 128/348.1 |
| 4,771,776 | 9/1988 | Powell et al. ..................... 128/344 |
| 4,820,349 | 4/1989 | Saab .................................. 128/344 |
| 4,941,877 | * 7/1990 | Montano ............................ 604/96 |
| 4,952,357 | 8/1990 | Euteneuer ......................... 264/129 |
| 5,087,246 | 2/1992 | Smith ................................. 604/96 |
| 5,147,302 | * 9/1992 | Euteneuer et al. .............. 604/103 |
| 5,350,361 | * 9/1994 | Tsukashima et al. ............ 606/194 |
| 5,456,666 | * 10/1995 | Campbell et al. ................. 604/96 |
| 5,458,572 | * 10/1995 | Campbell et al. ............... 606/194 |
| 5,672,169 | 9/1997 | Verbeek ............................... 606/1 |
| 5,759,172 | * 6/1998 | Weber et al. .................... 606/194 |
| 5,792,172 | * 8/1998 | Fischell et al. .................. 606/194 |
| 5,836,965 | * 11/1998 | Jendersee et al. .............. 606/194 |

FOREIGN PATENT DOCUMENTS

| | | |
|---|---|---|
| 3 124 198 | 6/1981 | (DE) . |
| 0 414 350 | 2/1991 | (EP) . |
| 2 078 114 | 1/1982 | (GB) . |

\* cited by examiner

Primary Examiner—Michael H. Thaler
(74) Attorney, Agent, or Firm—Heller Ehrman White & McAuliffe LLP

(57) ABSTRACT

A balloon catheter for dilating a stenotic region of a patient's body lumen such as an artery or for the implantation of an expandable stent within a patient's body lumen. The balloon of the catheter has a plurality of canted wings which are inclined at an angle of about 15° to about 75°, preferably about 30° to about 60° from a line tangent to an inner tubular member extending within the interior of the balloon.

17 Claims, 6 Drawing Sheets

CATHETER BALLOON WITH BIASED MULTIPLE WINGS

BACKGROUND OF THE INVENTION

This invention generally relates to balloon catheters, particularly balloon catheters for deploying stents, such as after percutaneous transluminal coronary angioplasty (PCTA) procedures.

In a typical PTCA procedure a dilatation balloon catheter is advanced over a guidewire to a desired location within the patient's coronary anatomy where the balloon of the dilatation catheter is properly positioned within a stenosis to be dilated. The balloon is inflated with radiopaque liquid at relatively high pressures (generally greater than 4 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

Very frequently the PTCA treatment modality includes the placement of a stent either simultaneously during the angioplasty or after a dilatation of a stenotic arterial region has been completed to provide long term lumen patency. Balloon catheters similar to those described above for dilatation are used to deploy stents within a patient's body lumen. Typically, an expandable stent is first disposed about the exterior of the deflated balloon on the distal extremity of the catheter in a constricted or otherwise unexpanded condition and then the catheter is advanced within the patient's body lumen until the stent mounted on the exterior of the balloon is at the location in which the stent is to be deployed, e.g. at the stenotic site of a previous dilatation. The balloon is inflated so as to expand the constricted or otherwise unexpanded stent against the wall defining the body lumen and then the balloon is deflated and the catheter withdrawn from the patient's body lumen. The expanded stent remains at the lumen site in an expanded condition when the catheter is removed.

Advances in material development for relatively non-compliant balloons designed for both dilatation and stent deployment have increased the tensile strength of the balloons allowing thinner balloon walls and thus lower catheter profiles. However, to obtain the benefits of a lower catheter profile, the wings which form when such balloons are deflated are wrapped around the inner member which extends through the interior of the balloon. The wrapped balloon may be covered with a protective sheath at least for handling and storage. Frequently, for stent delivery balloons, the stent is crimped onto a protective sheath covering which is somewhat elastically expansive so as to provide a more uniform expansion of the stent mounted on the sheath. The wrapped wings of the balloon are usually heat set in this condition so that the wings have a memory of the small wrapped dimensions when the balloon is deflated after inflation, e.g. for prepping, dilatation or stent deployment.

While some improvement in balloon profile has been obtained with the prior wrapped balloons, the procedures for forming the balloon with the desired memory complicates the manufacturing procedure and the use of the balloon. What has been needed is a catheter structure which simplifies the wrapping and eliminates the folding of the balloon wings and the heat setting thereof. The present invention satisfies these and other needs.

SUMMARY OF THE INVENTION

This invention is directed to a catheter having a balloon on a distal extremity of the catheter shaft which has a plurality of biased wings and to the method of forming the biased wings on the balloon.

The inflatable balloon on the catheter of the invention generally has a plurality of canted wings, each of which have been formed so as to be inclined at an angle of about 15° to about 75°, preferably about 30° to about 60°, with respect to a tangent line extending from the exterior of an inner member about which the wings are wrapped. The wings are formed of the cylindrical and part of the tapered ends of the balloon thus significantly reducing the balloon profile.

The inclined or canted wings are formed by pressing suitable shaping tools against the exterior of the balloon while the balloon is inflated at relatively low pressures of about 5 to about 20 psi, preferably about 8 to about 15 psi and, once the wings have been formed by the shaping tool, the interior of the balloon is subjected to a partial vacuum, i.e. a pressure of about 10 to about 29 inches (25.4–73.7 cm) of Hg, preferably about 20 to about 27 inches (51–68.6 cm) of Hg. in order to maintain the balloon in the constricted deflated condition with the canted wings of the balloon inclined and partially wrapped. The canted wings can be more easily wrapped around an inner tubular member extending within the balloon interior to reduce the effective profile of the balloon. The wrapping may be performed manually or by placing the balloon within an appropriate die and rotating either the balloon or the die or both to wrap the wings. A variety of other methods may be employed to wrap the balloons.

The vacuum applied within the balloon interior holds the canted wings in a wrapped position long enough so that a sheath or a stent can be mounted about the wrapped wings of the balloon. A stent may also be slid over and crimped onto the sheath for subsequent deployment. The angularity of the wings with respect to a line tangent to the exterior of the inner member greatly facilitates the wrapping of the wings and the reforming thereof when the deflated balloon is pulled back into a sheath or the distal end of a guiding catheter.

Details of stents suitable for use with the present invention can be found in U.S. Pat. No. 5,344,426, U.S. Pat. No. 5,423,885, U.S. Pat. No. 5,441,515, U.S. Pat. No. 5,443,458, U.S. Pat. No. 5,443,500 and U.S. Pat. No. 5,514,154, all of which are assigned to the present assignee. They are incorporated herein by reference. Other stent designs may also be employed.

In one aspect of the invention, the catheter has an elongated shaft with a proximal end, a distal end, a port in the distal end and guidewire lumen extending through at least the distal portion of the catheter to and in fluid communication with the port in the distal end of the catheter shaft. The balloon of the invention may be mounted on a distal extremity of the catheter shaft in a conventional fashion with a distal skirt secured by fusion bonding or a suitable adhesive to a distal extremity of the inner tubular member extending through the interior of the balloon and a proximal skirt of the balloon is similarly secured to a portion of the catheter shaft which may be the distal extremity of an outer tubular member which in part forms the catheter shaft.

The balloon may be made from suitable thermoplastic polymeric materials including high density polyethylene, polyethylene terephthalate (PET), polyamide (e.g. nylon 11 or 12), ionomers such as Surlyn sold by DuPont, polyurethane and polyamide block co-polymers such as PEBAX.

The present invention provides an intralumenal catheter with an improved balloon member with multiple wrapped wings which are formed so as to be inclined to predispose the wings to wrapping and subjected to an interior vacuum to hold the wings in the constricted condition. The crease which forms with the wing formation extend well into the tapered ends of the balloon which facilitates mounting a sheath or stent onto the wrapped balloon. A stent may be mounted and then crimped directly onto the wrapped balloon or onto a sheath covering the wrapped balloon for vascular deployment. The inclined wings also facilitate the pullback of the deflated balloon after a vascular or other procedure into the distal tip of the guiding catheter.

Long term disposition of the balloon in the wrapped condition and/or thermal treatment of the wrapped balloon effect a set which the balloon tends to stay in for the duration of storage and use.

These and other advantages of the invention will become more apparent from the following detailed description of the invention when taken in conjunction with the accompanying exemplary drawings.

DETAILED DESCRIPTION OF THE INVENTION

Figure 1:
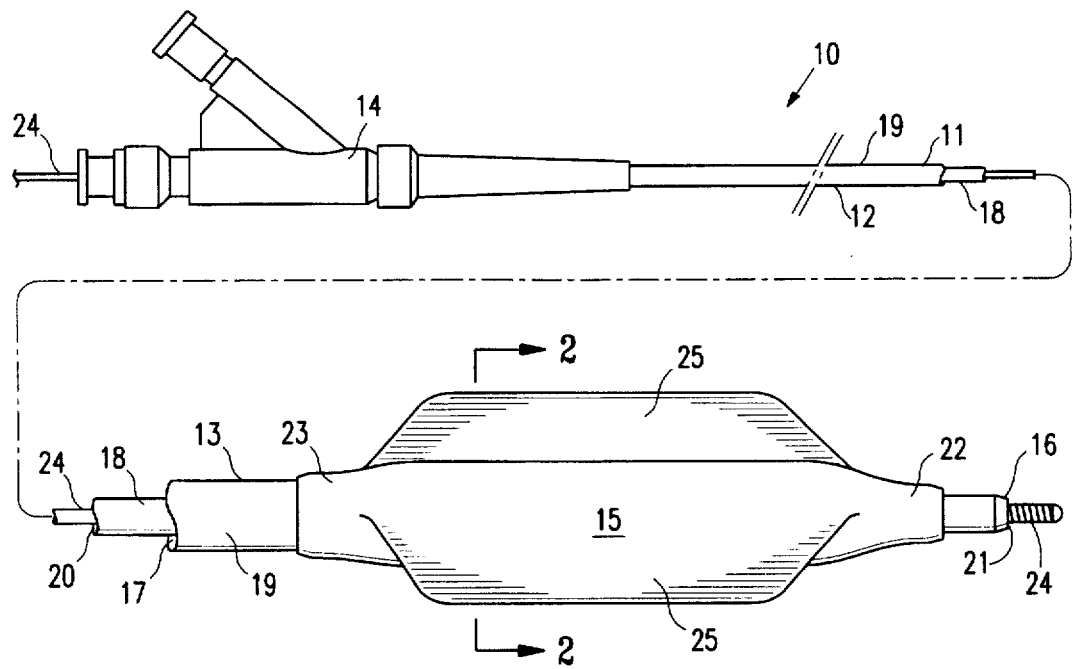
FIG. 1 is an elevational schematic view, partially in section, of a balloon catheter embodying features of the invention.
Figure 2:
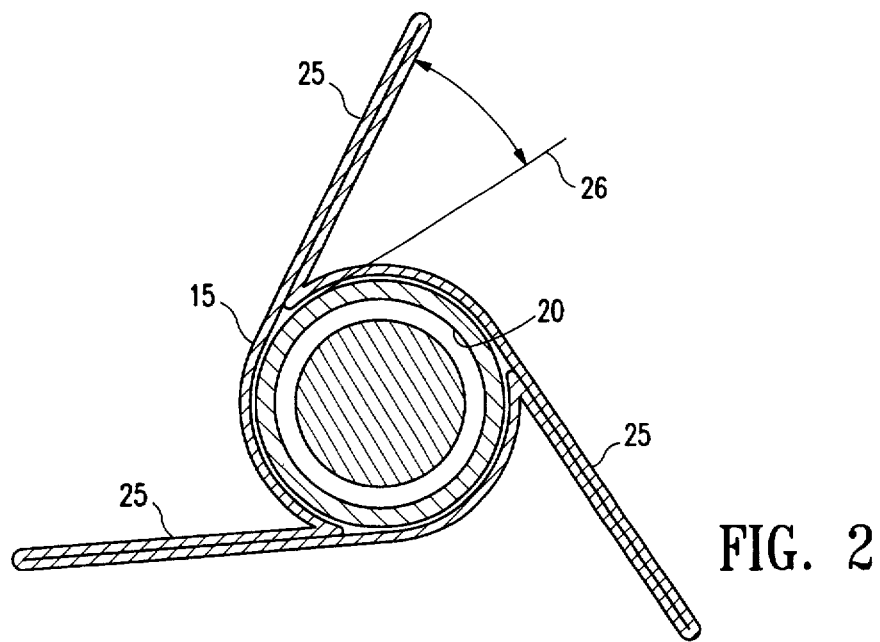
FIG. 2 is a transverse cross-sectional view of the catheter shown in FIG. 2 taken along the lines 2—2.

Reference is made to FIGS. 1–2 which illustrate a balloon catheter 10 embodying features of the invention. Catheter 10 has an elongated shaft 11 with proximal and distal shaft sections 12 and 13, a multiarm adapter 14 on the proximal end of the shaft and an expandable balloon 15 on the distal shaft section spaced proximal to the distal end 16. An inflation lumen 17 extends between the proximal end of shaft 11 and a location spaced proximal to the distal end 16 and is in fluid communication with the interior of the balloon 15. The catheter shaft 11 is provided with an inner tubular member 18 and an outer tubular member 19 of suitable polymeric material. A guidewire receiving lumen 20 extends through the proximal and distal shaft sections 12 and 13 to the port 21 in the distal end 16. In the distal shaft section 13, the guidewire receiving lumen 20 is defined at least in part by the inner tubular member 18.

The balloon 15 has a distal skirt 22 which is secured by suitable means such as fusion or adhesive bonding to an exterior portion of the inner tubular member 18 and a proximal skirt 23 which is secured by the same or similar means to the distal end of the outer tubular member 19. A guidewire 24 is slidably disposed within the guidewire lumen 20.

As shown more clearly in FIG. 2, the balloon 15 has a plurality of canted wings 25 which are deformed so as to be inclined at a suitable angle with respect to a line 26 which is approximately tangent with the exterior surface of the inner tubular member 18.

Figure 3:
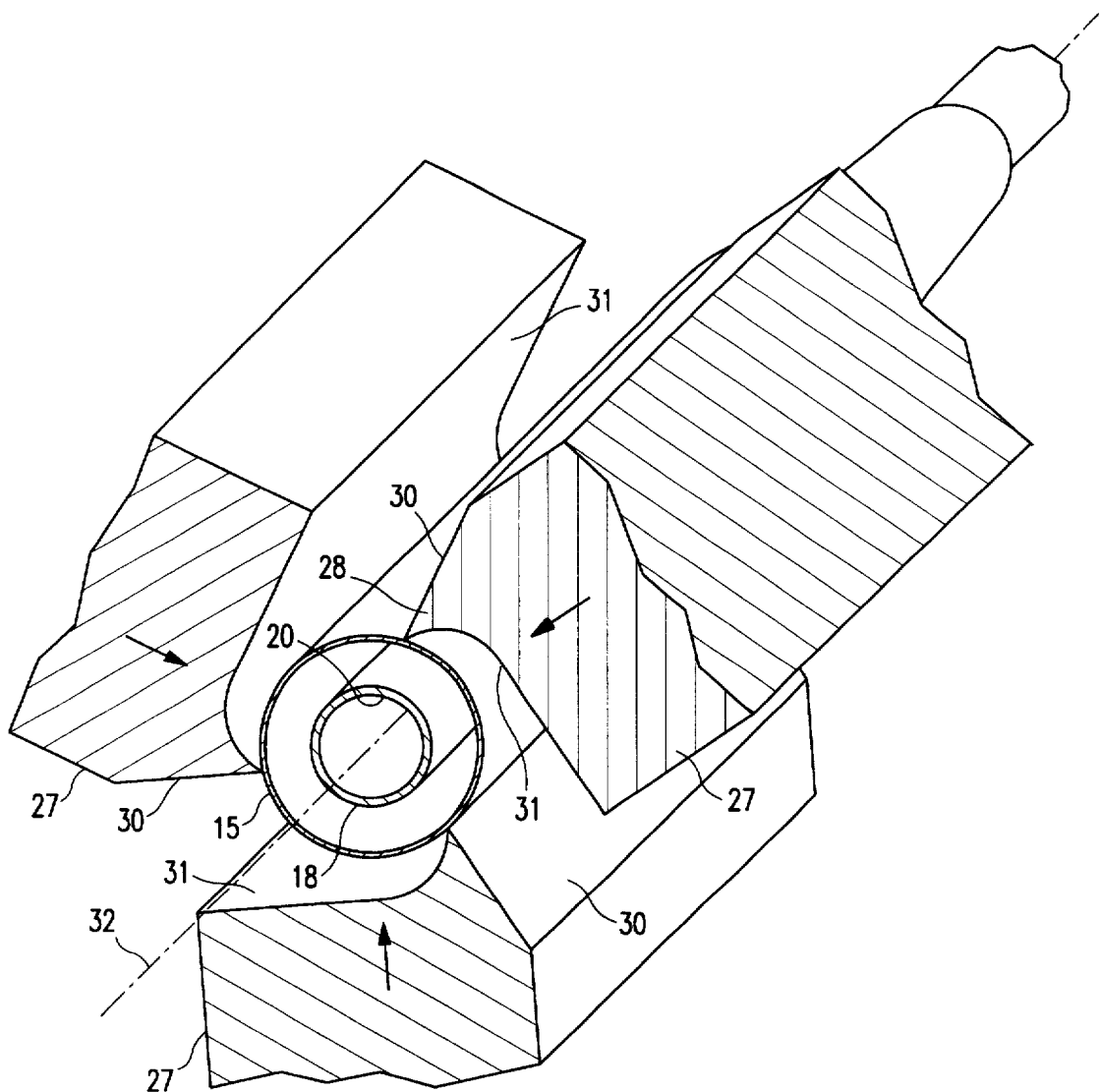
FIGS. 3 and 4 schematically illustrate the forming of multiple canted wings on the balloon.
Figure 4:
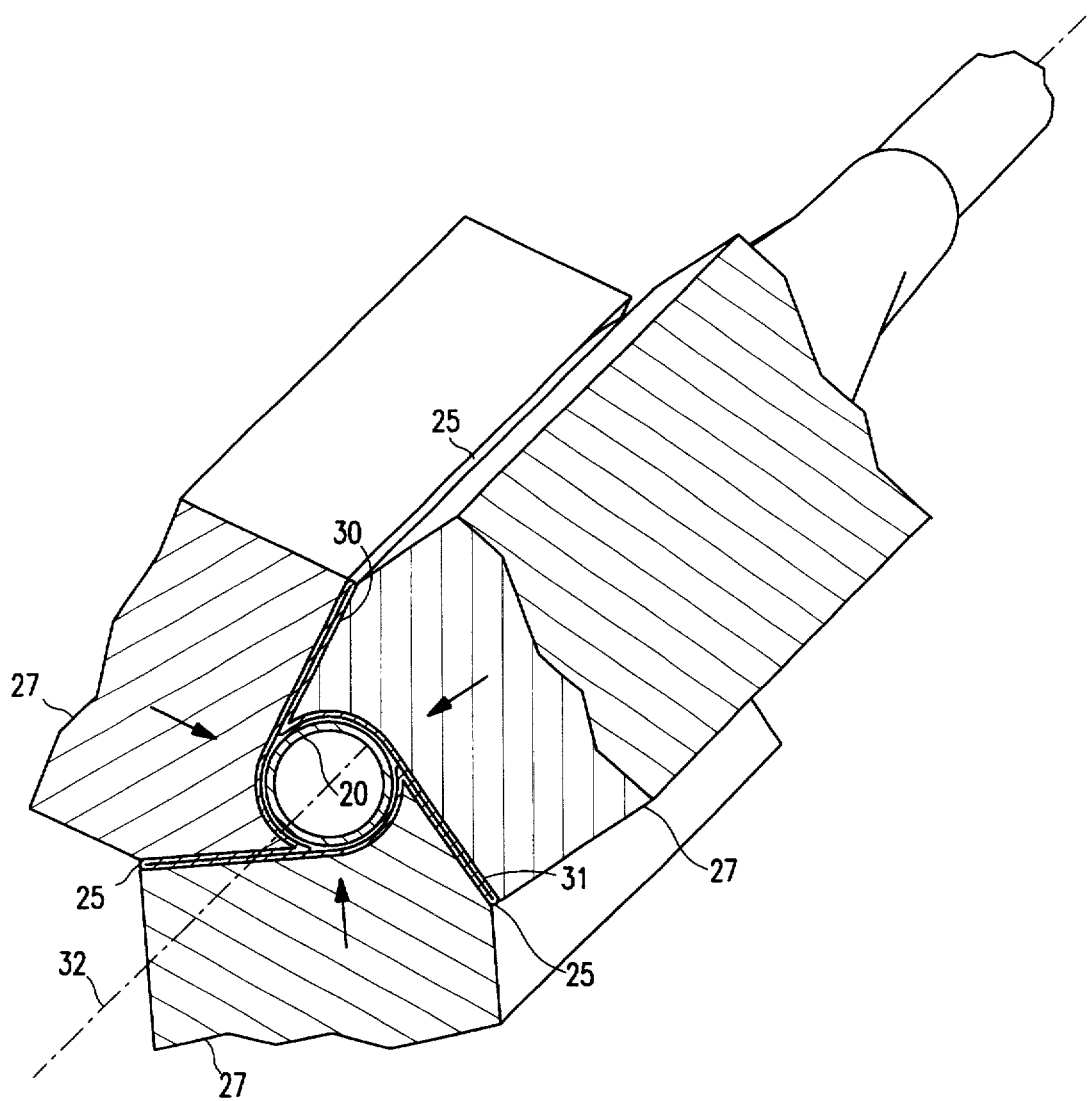

FIGS. 3 and 4 schematically illustrate the deformation of the balloon 15 so as to form the canted wings 25. As shown in FIG. 3, a partially inflated balloon 15 (e.g. inflated to an internal pressure of about 5–15psi) is surrounded by three elongated shaping tools 27. Each of the shaping tools 27 has planar surfaces 30 and 31 and may have an elongated wedge-like deforming element 28 as shown in the drawings. The surface 31 of one shaping tool 27 is configured to press against the underside of a first canted wing 25 and the surface 30 of the same shaping tool is configured to press against the top side of a second canted wing 26 adjacent to the first canted wing. The shaping tools 27 are assembled so that when they are moved radially inwardly the wedge-like deforming elements 28 thereof are off-set from the longitudinal axis 32 as shown to deform the canted wing 25 in the desired manner.

Figure 5:
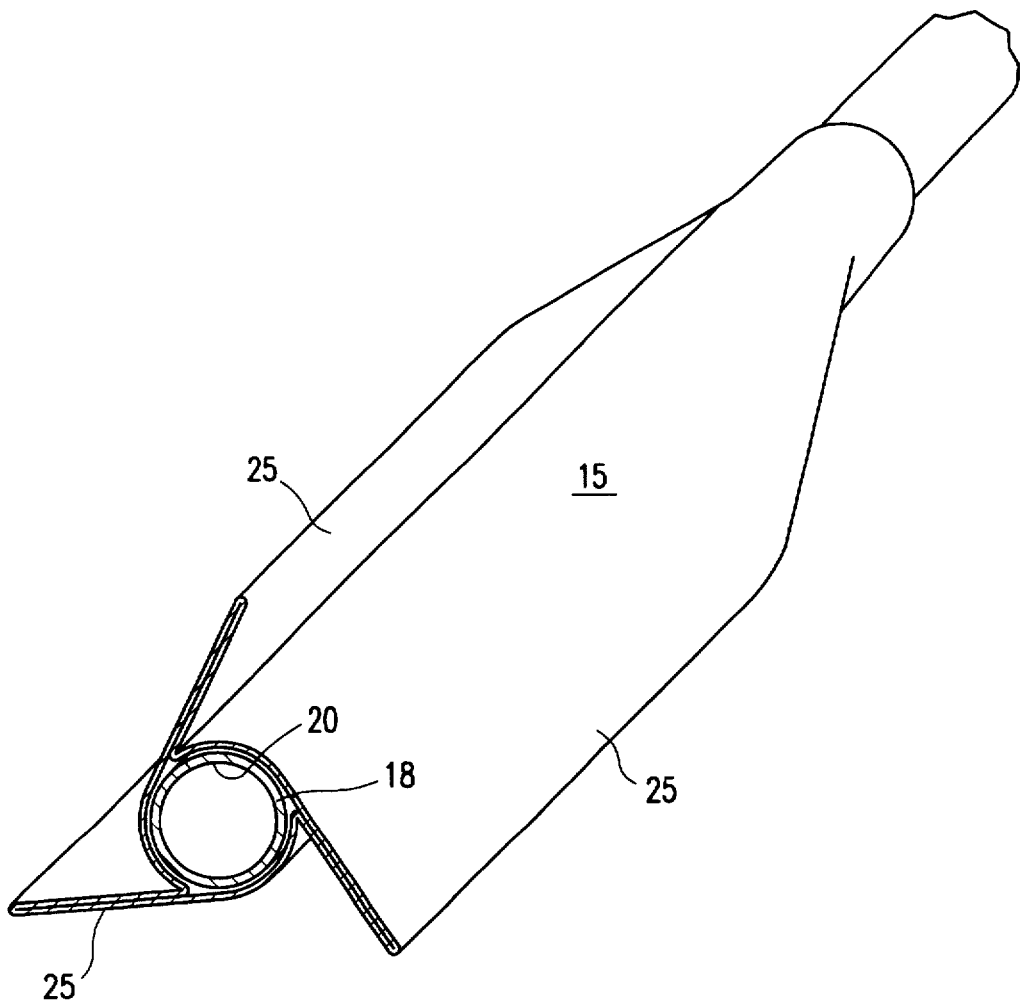
FIG. 5 is a perspective view in section which illustrates the balloon with multiple canted wings.

While the balloon 15 is inflated at low pressures, the shaping tools 27 are moved inwardly until the surfaces 30 of the shaping tools are pressed against the bottom side of the canted wings 25 and the surfaces 31 of the adjacent shaping tools are pressed against the top side of the wings as shown in FIG. 4. A space of about 0.004 to about 0.008 inch is maintained between the surfaces 30 and 31 but these surfaces do press against the balloon material between these surfaces to form the wings. There is little or no deformation of the outer tip of the wings, i.e. there is no folding as was done in the prior art. The interior of the balloon 15 is then subjected to a partial vacuum which holds the canted wings 25 in a partially wrapped condition as shown in FIGS. 2 and 5.

Figure 6:
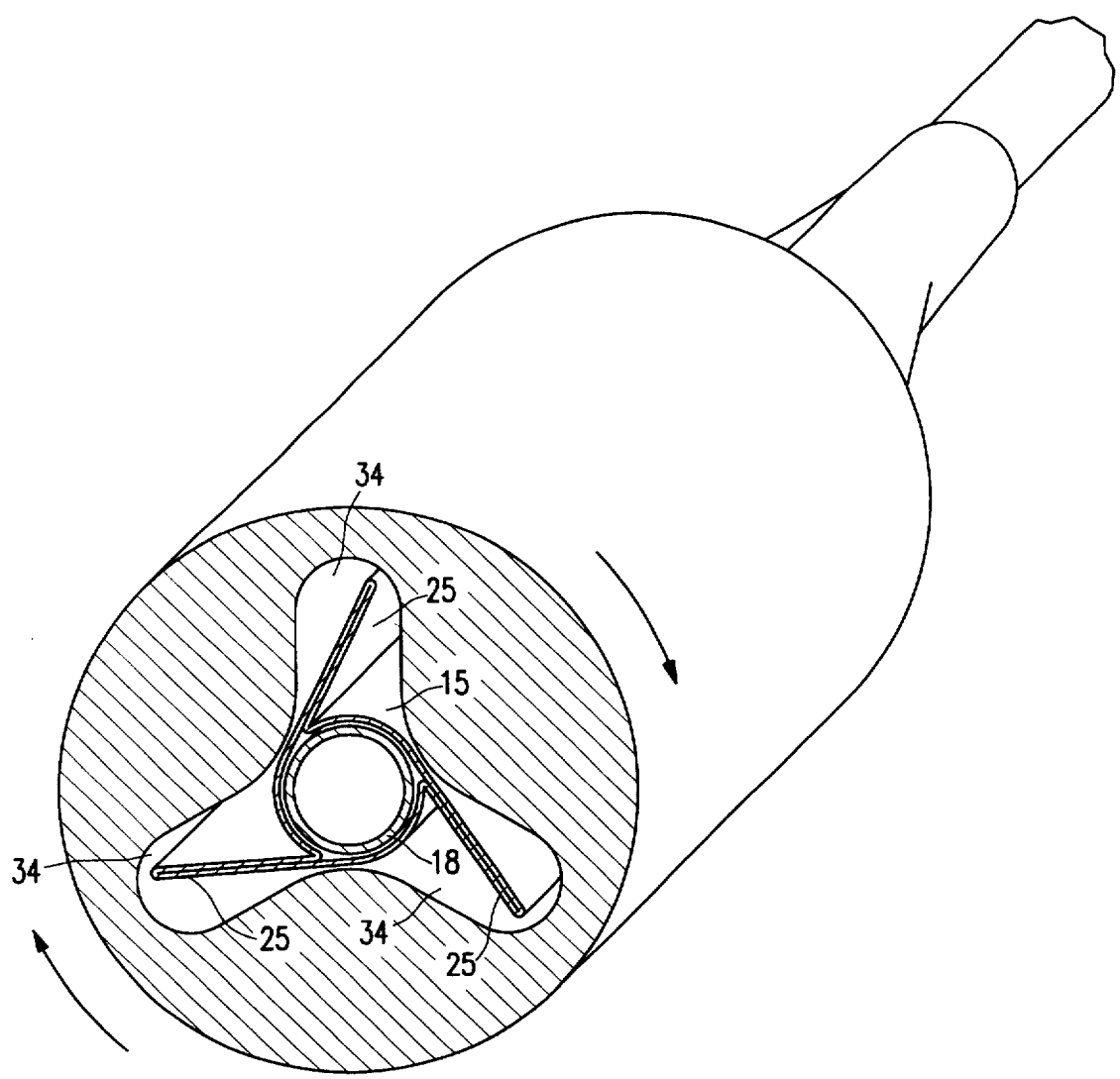
FIG. 6 illustrates the placement of the balloon with multiple canted wings within a die for wrapping the canted wings about an inner tubular member.
Figure 7:
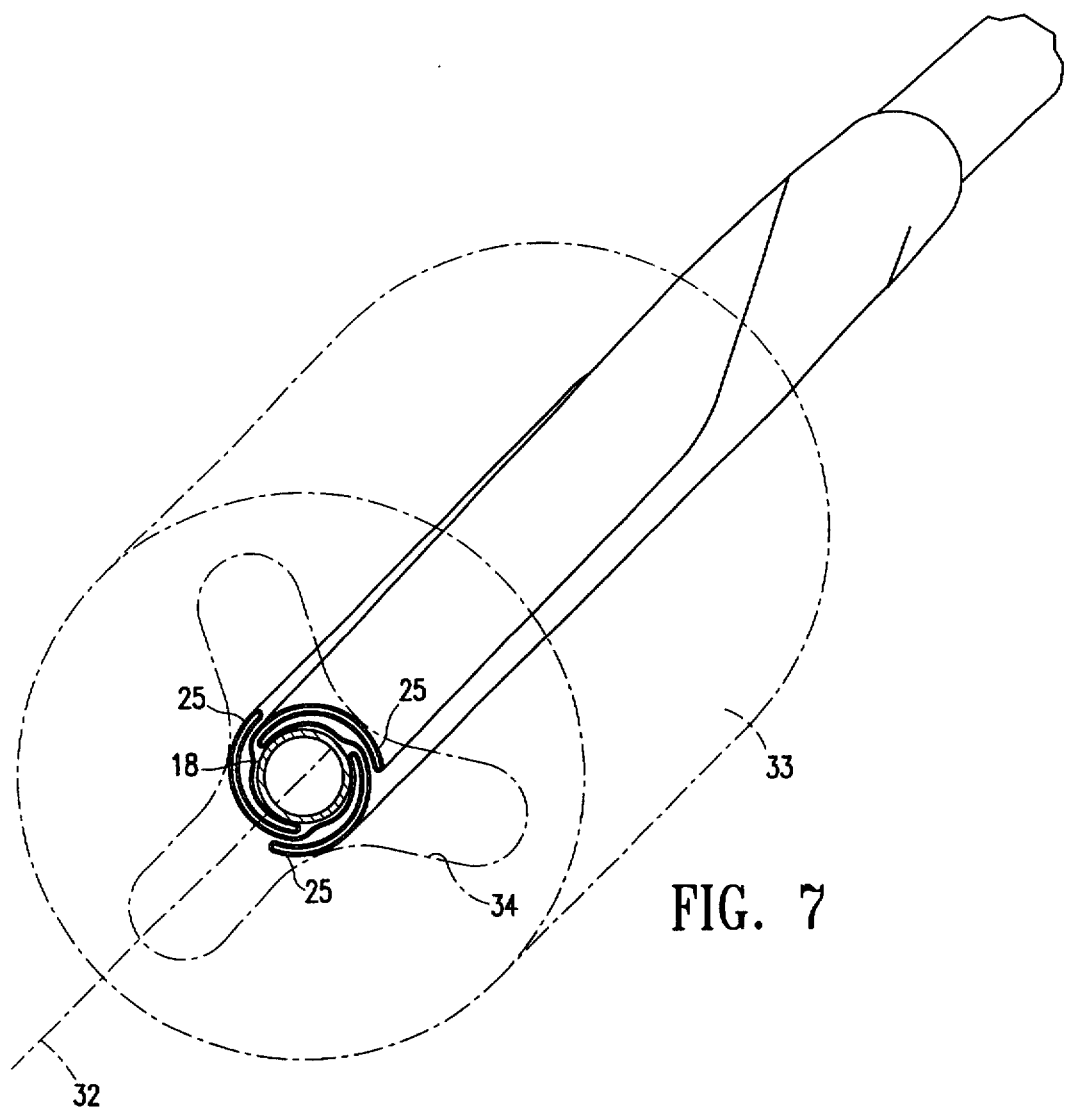
FIG. 7 illustrates the balloon in the wrapped condition within the die.
Figure 8:
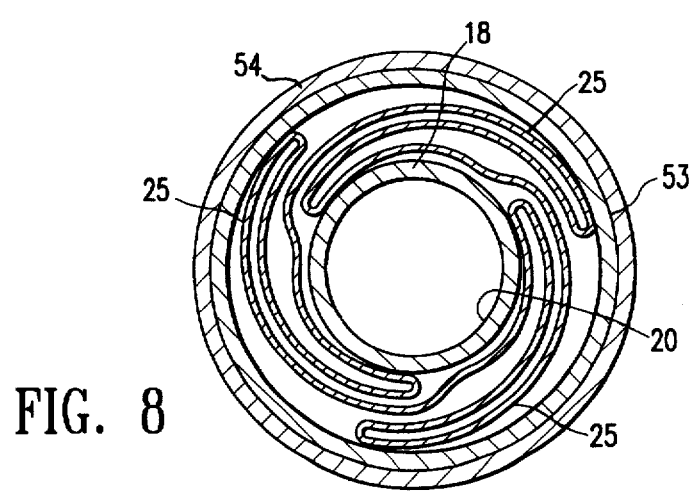
FIG. 8 is a transverse cross-sectional view which illustrates a stent disposed about the multiwinged balloon shown in FIGS. 1–2.

The canted wings 25 of balloon 15 may be wrapped about the inner tubular member 18 by placing the distal extremity of the catheter 10 within a die 33 so that the canted wings 25 of the balloon 15 are disposed within the chambers 34 of the die as shown in FIG. 6. Relative rotational motion is effected between the die 33 and the distal extremity of the catheter 10 so that the canted wings 25 disposed within the chambers 34 are wrapped about the inner tubular member 18 as shown in FIG. 7. When wrapped, the tips of the wings may extend over an adjacent wrapped wing depending upon the lengths of the wings and the diameter of the inner tubular member 18 about which the wings are wrapped. Once wrapped, the canted wings 25 have little tendency to unwrap particularly when subjected to an internal vacuum, so a stent 54 may be readily slid over and crimped over the wrapped balloon 15 as shown in FIG. 8. Typically, when the stent 54 is disposed about the balloon 15, it is crimped onto the exterior of the balloon 15 to facilitate the introduction of the catheter into a patient's vascular system, but a protective sheath 53 may be applied to the exterior of the balloon and the stent 54 crimped onto the sheath.

When the balloon 15 is in the desired location within the patient's vascular system, inflation fluid is introduced into the interior of the balloon through the inflation lumen 17 to inflate the balloon and expand the stent 54 crimped onto the balloon. Because of the multiple canted wings 25 on the balloon 15, when the balloon inflates, it readily and uniformly expands the stent 54 mounted onto the balloon. Once expanded, the stent 54 is secured within the body lumen and the balloon may then be deflated and withdrawn.

While the balloon catheter with canted wings has been described herein as a stent delivery catheter, those skilled in the art will recognize that the catheter may be employed as a balloon angioplasty catheter to dilate stenosis within a patient's coronary artery or other body lumen. When employed as a balloon angioplasty catheter, a sheath may be provided about the balloon with canted wings to hold the canted wings in place. Other modifications and improvements may be made to the invention without departing from the scope thereof.

What is claimed is:

1. A balloon catheter, comprising:
   a) an elongated shaft having proximal and distal ends, a port in the distal end, an inner tubular member defining at least in part a guidewire lumen extending to and in fluid communication with the port in the distal end and an inflation lumen extending to a location spaced proximal to the distal end; and
   b) an inflatable deflated balloon on a distal portion of the elongated shaft and having an interior in fluid communication with the inflation lumen and having a first unwrapped configuration and a second wrapped configuration when the balloon is wrapped around the inner tubular member, the balloon in the first unwrapped configuration having a plurality of canted wings, each of which is formed to have a base inclined at an angle of about 15° to about 75° from a line at the base of said wing tangent to an exterior surface of the inner member, the angle being measured in a cross-sectional plane which is perpendicular to the longitudinal axis of said elongated shaft, and the balloon in the second wrapped configuration having a curvilinear junction between the base of the wing and a balloon section located between the wing and an adjacent wing.

2. The catheter of claim 1 wherein the balloon has at least three canted wings.

3. The catheter of claim 1 wherein the balloon is formed of a thermoplastic polymeric material.

4. The catheter of claim 3 wherein the thermoplastic polymeric material is selected from the group consisting of polyolefins, polyesters, polyamide, polyurethanes and copolymers and blends thereof.

5. The catheter of claim 1 wherein the interior of the balloon is at a partial vacuum of about 10 to about 29 inches of Hg.

6. The catheter of claim 1 wherein the interior of the balloon is at a partial vacuum of about 20 to about 27 inches of Hg.

7. The catheter of claim 1 wherein the base of each wing of the balloon is inclined at an angle of about 30° to about 60° from the line at the base of said wing.

8. A method of forming a low profile balloon formed of relatively non-compliant polymeric material having a plurality of wings canted at an angle comprising:
   a) providing a balloon having a cylindrical working section and tapered ends which define an interior chamber within the balloon and an elongated tubular inner member extending within the interior chamber of the balloon;
   b) inflating the balloon to a pressure of less than 20 psi;
   c) pressing a plurality of shaping surfaces against the exterior of the inflated balloon so as to form a plurality of wings, each wing having a base inclined at an angle of about 15° to about 75° from a line at the base of said wing tangent to an exterior surface of the inner member;
   d) subjecting the interior chamber of the balloon to a partial vacuum of about 10 to about 29 inches of Hg; and
   e) wrapping the wings about an inner member.

9. The method of claim 8 wherein at least three shaping members are pressed against the exterior of the partially inflated balloon.

10. The method of claim 8 wherein the vacuum applied within the interior of the balloon is about 20 to about 27 inches of Hg.

11. A method of mounting a cylindrically shaped stent onto cylindrically shaped balloon on a stent delivery catheter, comprising:
   a) providing a stent delivery catheter having proximal and distal portions and a balloon on the distal portion having a cylindrical working section and tapered ends which define an interior chamber within the balloon and an elongated inner member extending within the interior chamber of the balloon;
   b) inflating the balloon to a relatively low pressure;
   c) pressing a plurality of shaping surfaces against the exterior of the partially inflated balloon so as to form a plurality of wings each wing having a base inclined at an angle of about 15° to about 75° from a line at the base of said wing tangent to an exterior surface of the inner member; and
   d) reducing the pressure within the interior chamber of the balloon to a vacuum of about 10 to about 29 inches of Hg so as to maintain the balloon wings in the desired inclined position;
   e) wrapping the wings about the balloon in the same directions as the wings are inclined;
   f) mounting a stent about the wrapped balloon; and
   g) crimping the stent onto the wrapped balloon.

12. The method of claim 11 wherein a vacuum of about 20 to about 27 inches of Hg is applied to the interior of the balloon.

13. A stent delivery system, comprising:
   a) a catheter with an elongated shaft having proximal and distal ends, a port in the distal end, an inner tubular member defining at least in part a guidewire lumen extending to and in fluid communication with the port in the distal end and an inflation lumen extending to a location spaced proximal to the distal end, and an inflatable deflated balloon on a distal portion of the elongated shaft and having an interior in fluid communication with the inflation lumen and having a first unwrapped configuration and a second wrapped configuration when the balloon is wrapped around the inner tubular member, the balloon in the first unwrapped configuration having a plurality of canted wings, each of which is formed to have a base inclined at an angle of about 15° to about 75° from a line at the base of said wing tangent to an exterior surface of the inner member, the angle being measured in a cross-sectional plane which is perpendicular to the longitudinal axis of said elongated shaft, and the balloon in the second wrapped configuration having a curvilinear junction between the base of the wing and a balloon section located between the wing and an adjacent wing; and
   b) an expandable stent mounted on the exterior of the balloon.

14. The stent delivery system of claim 13 wherein a sheath is disposed between the exterior of the balloon and the stent mounted thereon.

15. A balloon catheter comprising:
   a) an elongated shaft having proximal and distal ends, a port in the distal end, an inner tubular member defining at least in part a guidewire lumen extending to and in fluid communication with the port in the distal end and an inflation lumen extending to a location spaced proximal to the distal end; and b) an inflatable deflated balloon on a distal portion of the elongated shaft which has an interior in fluid communication with the inflation lumen and which has a plurality of canted wings, each of which is formed to have a base inclined at an angle of about 15° to about 75° from a line at the base of said wing tangent to an exterior surface of the inner member, the angle being measured in a cross-sectional plane which is perpendicular to the longitudinal axis of said elongated shaft, and wherein each of the wings is substantially straight as viewed in a cross-section taken perpendicular to the longitudinal axis of said elongated shaft.

16. A stent delivery system comprising:

a) a catheter with an elongated shaft having proximal and distal ends, a port in the distal end, an inner tubular member defining at least in part a guidewire lumen extending to and in fluid communication with the port in the distal end and an inflation lumen extending to a location spaced proximal to the distal end, and an inflatable deflated balloon on a distal portion of the elongated shaft which has an interior in fluid communication with the inflation lumen and which has a plurality of canted wings, each of which is formed to have a base inclined at an angle of about 15° to about 75° from a line at the base of said wing tangent to an exterior surface of the inner member, the angle being measured in a cross-sectional plane which is perpendicular to the longitudinal axis of said elongated shaft, and wherein each of the wings is substantially straight as viewed in a cross-section taken perpendicular to the longitudinal axis of said elongated shaft; and b) an expandable stent mounted on the exterior of the balloon.

17. A balloon catheter, comprising:

a) an elongated shaft having proximal and distal ends, a port in the distal end, an inner tubular member defining at least in part a guidewire lumen extending to and in fluid communication with the port in the distal end and an inflation lumen extending to a location spaced proximal to the distal end; and b) an inflatable deflated balloon on a distal portion of the elongated shaft and having an interior in fluid communication with the inflation lumen and having a first unwrapped configuration and a second wrapped configuration when the balloon is wrapped around the inner tubular member, the balloon in the first unwrapped configuration having a plurality of canted wings, each of which is formed to have a base inclined at an angle of about 15° to about 75° from a line at the base of said wing tangent to an exterior surface of the inner member, the angle being measured in a cross-sectional plane which is perpendicular to the longitudinal axis of said elongated shaft.

* * * * *